United States Patent
Zhou et al.

(10) Patent No.: US 11,275,037 B2
(45) Date of Patent: Mar. 15, 2022

(54) ALLOY POWDER CLEANLINESS INSPECTION USING COMPUTED TOMOGRAPHY

(71) Applicant: General Electric Company, Schenectady, NY (US)

(72) Inventors: Ying Zhou, Niskayuna, NY (US); Evan Dolley, Niskayuna, NY (US); Anjali Singhal, Niskayuna, NY (US); Albert Cerrone, Notre Dame, IN (US); Daniel Ruscitto, Niskayuna, NY (US); Rajiv Sampath, West Chester, OH (US); Martin Morra, Niskayuna, NY (US); Krzysztof Lesnicki, Asheville, NC (US); Paul Roth, West Chester, OH (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 363 days.

(21) Appl. No.: 16/681,053

(22) Filed: Nov. 12, 2019

(65) Prior Publication Data
US 2020/0182808 A1   Jun. 11, 2020

Related U.S. Application Data

(60) Provisional application No. 62/776,724, filed on Dec. 7, 2018.

(51) Int. Cl.
*G01N 23/00* (2006.01)
*G01N 23/203* (2006.01)
(Continued)

(52) U.S. Cl.
CPC ............. *G01N 23/046* (2013.01); *G06T 7/10* (2017.01); *G06T 11/003* (2013.01); *G06T 17/20* (2013.01);
(Continued)

(58) Field of Classification Search
CPC ......... G06T 7/10; G06T 17/20; G06T 11/003; G06T 2207/10081; G06T 17/10;
(Continued)

(56) References Cited

U.S. PATENT DOCUMENTS 6,438,261 B1   8/2002  Moshe et al.
6,536,944 B1   3/2003  Archibald et al.
(Continued)

*Primary Examiner* — Irakli Kiknadze
(74) *Attorney, Agent, or Firm* — Buckley, Maschoff & Talwalkar LLC

(57) ABSTRACT

A system and method are provided including an inclusion module to receive a powder sample from a powder source; a computed tomography equipment; a memory for storing program instructions; an inclusion processor, coupled to the memory, and in communication with the inclusion module, and operative to execute program instructions to: receive the powder sample; execute a computed tomography (CT) scan process of the received sample to generate a first dataset including one or more images; identify inclusions in the one or more images, via a segmentation process; reconstruct, via a reconstruction process, the identified inclusion into a 3D representation; measure the identified inclusion; mark the inclusions on one or more image slices from the 3D representations; and determine whether the powder source is contaminated based on the one or more marked images. Numerous other aspects are provided.

20 Claims, 4 Drawing Sheets

(51) Int. Cl.
*G01N 23/046* (2018.01)
*G06T 7/10* (2017.01)
*G06T 11/00* (2006.01)
*G06T 17/20* (2006.01)

(52) U.S. Cl.
CPC ... *G01N 2223/419* (2013.01); *G01N 2223/62* (2013.01); *G06T 2207/10081* (2013.01)

(58) Field of Classification Search
CPC ....... G06T 7/0004; G06T 7/62; G06T 11/008; G06T 7/174; G06T 17/00; G06T 7/0012; G06T 7/50; G06T 7/12; G06T 7/33; G06T 15/08; G06T 7/11; G06T 19/00; G01N 23/046; G01N 2223/62; G01N 2223/419; G01N 2223/03; G01N 2223/312; G01N 2223/33; G01N 15/0227; G01N 13/00; G01N 13/02; G01N 33/246; G01N 1/28; G01N 15/088; G01N 33/20; G01N 23/2251; G06F 40/40; G06F 40/20; G16H 50/20; G16H 30/40; G16H 50/30; G06K 9/00208; G06K 9/6282; G06K 9/3233; G06K 9/66; G06K 9/34; A61B 6/5211; A61B 6/032; A61B 17/3403; A61B 34/30; A61B 10/0266; A61B 90/11; A61B 17/68; A61B 17/866; A61B 34/10; A61B 34/00; A61B 6/4405; A61B 6/5241; A61B 6/5217; A61B 5/7425; A61B 6/584; A61B 6/547; A61B 6/487; A61B 6/463; A61B 5/066; A61B 6/505; A61B 6/022; A61B 5/1114; A61B 34/20; A61B 5/055; A61B 5/4566; A61N 5/1039; A61N 5/103; G06N 3/0454; G06N 3/08; G01R 33/4835
USPC ................................................. 378/4, 19, 75
See application file for complete search history.

(56) References Cited

U.S. PATENT DOCUMENTS

| | | | |
|---|---|---|---|
| 6,813,338 B2 * | 11/2004 | Takata | G01N 23/2076 378/75 |
| 7,184,141 B2 | 2/2007 | Brewer et al. | |
| 7,813,523 B1 | 10/2010 | Larsson | |
| 8,160,305 B2 | 4/2012 | Laurint et al. | |
| 8,401,239 B2 | 3/2013 | Porikli et al. | |
| 8,538,119 B2 | 9/2013 | Taki et al. | |
| 2012/0163547 A1 * | 6/2012 | Lee | G21K 1/062 378/120 |
| 2015/0331145 A1 | 11/2015 | Grachev et al. | |
| 2015/0356730 A1 * | 12/2015 | Grove | G06T 7/64 382/124 |
| 2018/0058995 A1 | 3/2018 | Hamann et al. | |
| 2018/0321393 A1 * | 11/2018 | Wu | C01G 25/006 |
| 2021/0004507 A1 * | 1/2021 | Yamazaki | B22F 10/80 |

* cited by examiner

ALLOY POWDER CLEANLINESS INSPECTION USING COMPUTED TOMOGRAPHY

CROSS REFERENCE TO RELATED APPLICATION

The present application claims priority from the following U.S. Provisional patent application, which is hereby incorporated by reference herein in its entirety for all purposes: U.S. Provisional Patent Application Ser. No. 62/776,724, filed Dec. 7, 2018, and entitled "ALLOW POWDER CLEANLINESS INSPECTION USING COMPUTED TOMOGRAPHY".

BACKGROUND

Powder metals may be used to create various components of industrial assets or equipment. These powder metals may be alloys (i.e., mixtures of two or more metallic elements). The alloy powder may include some level of nonmetallic inclusions that are intrinsic to the production process, or contaminants arising from inadequate maintenance of production equipment. Excessive occurrence of either may be detrimental to the properties of the material made from the powder, and limits must be set and maintained on their occurrence. The mechanical capability of an alloy may be limited by the level of defects. Bulk chemical analysis may not be effective to separate the contaminants due to the extremely low concentrations of the contaminant particles. A current method to quantify alloy powder contamination is by Heavy Liquid Separation (HLS). However, HLS is limited to contaminant particles with lower densities than the heavy liquid.

It would be desirable to provide systems and methods to improve defect detection in alloy powders.

SUMMARY

According to some embodiments, a system is provided including an inclusion module to receive a powder sample from a powder source; a computed tomography equipment; a memory for storing program instructions; an inclusion processor, coupled to the memory, and in communication with the inclusion module, and operative to execute program instructions to: receive the powder sample; execute a computed tomography (CT) scan process of the received sample to generate a first dataset including one or more 2D images; identify inclusions in the one or more 2D images, via a segmentation process; reconstruct, via a reconstruction process, the identified inclusion into a 3D representation; measure the identified inclusion; mark the inclusions on one or more 2D image slices from the 3D representations; and determine whether the powder source is contaminated based on the one or more marked images.

According to some embodiments, a method is provided including receiving the powder sample; executing a computed tomography (CT) scan process of the received sample to generate a first dataset including one or more 2D images; identifying inclusions in the one or more 2D images, via a segmentation process; reconstructing, via a reconstruction process, the identified inclusion into a 3D representation; measuring the identified inclusion; marking the inclusions on one or more 2D image slices from the 3D representations; and determining whether the powder source is contaminated based on the one or more marked images.

According to some embodiments a non-transient, computer-readable medium storing instructions to be executed by a processor to perform a method comprising: receiving the powder sample; executing a computed tomography (CT) scan process of the received sample to generate a first dataset including one or more 2D images; identifying inclusions in the one or more 2D images, via a segmentation process; reconstructing, via a reconstruction process, the identified inclusion into a 3D representation; measuring the identified inclusion; marking the inclusions on one or more 2D image slices from the 3D representations; and determining whether the powder source is contaminated based on the one or more marked images.

A technical effect of some embodiments of the invention is an improved and/or computerized technique and system for determining the presence of inclusions in a metal powder using computed tomography (CT), irrespective of the density of the inclusions. One or more embodiments provide for the assessment of metal alloy powder cleanliness (i.e., without contaminants). One or more embodiments provide for the assessment of contaminants that have different chemistries and densities from the bulk metal powder, such as oxide particles; which are shown to be sometimes present during examination by scanning electron microscopy and X-ray spectroscopy. It is noted that oxide particles may be expected to be present in metal powders in small amounts based on knowledge of how the powder is created and based on the presence of some oxide particles in samples. The presence of the oxide particles may be identified using X-ray spectroscopy in a scanning electron microscope, for example. One or more embodiments provide for an inclusion module that uses computed tomography and advanced image processing to quantitatively identify contaminant particles with densities both higher and lower than the bulk powder. One or more embodiments may provide an inclusion detection process that may be more effective than HLS, as it detects contaminant particles in the powder regardless of whether the density is higher or lower than the bulk powder, thereby finding more inclusions. The inclusion determining process provided in one or more embodiments also does not require the highly toxic chemical used in HLS and may be potentially faster. As used herein, the term "inclusion" and "defect" may be used interchangeably. It is noted that the 3D size and morphology representation of the contaminant particles provided by one or more embodiments, may be used directly for material capability models for turbine engine component life prediction. One or more embodiments may provide inclusion detection processes amenable for automation. One or more embodiments may provide for inclusion detection processes that are non-destructive and environmentally friendly, as no chemicals are used. One or more embodiments may provide for improved detection of inclusions which may result in more mechanically capable asset components produced from the powder metal. Other real-world benefits include providing a quality control method to evaluate metal powder cleanliness especially for Premium Quality Alloys used for Aircraft Rotating Parts, and other suitable parts.

With this and other advantages and features that will become hereinafter apparent, a more complete understanding of the nature of the invention can be obtained by referring to the following detailed description and to the drawings appended hereto.

Other embodiments are associated with systems and/or computer-readable medium storing instructions to perform any of the methods described herein.

DETAILED DESCRIPTION

Figure 1:
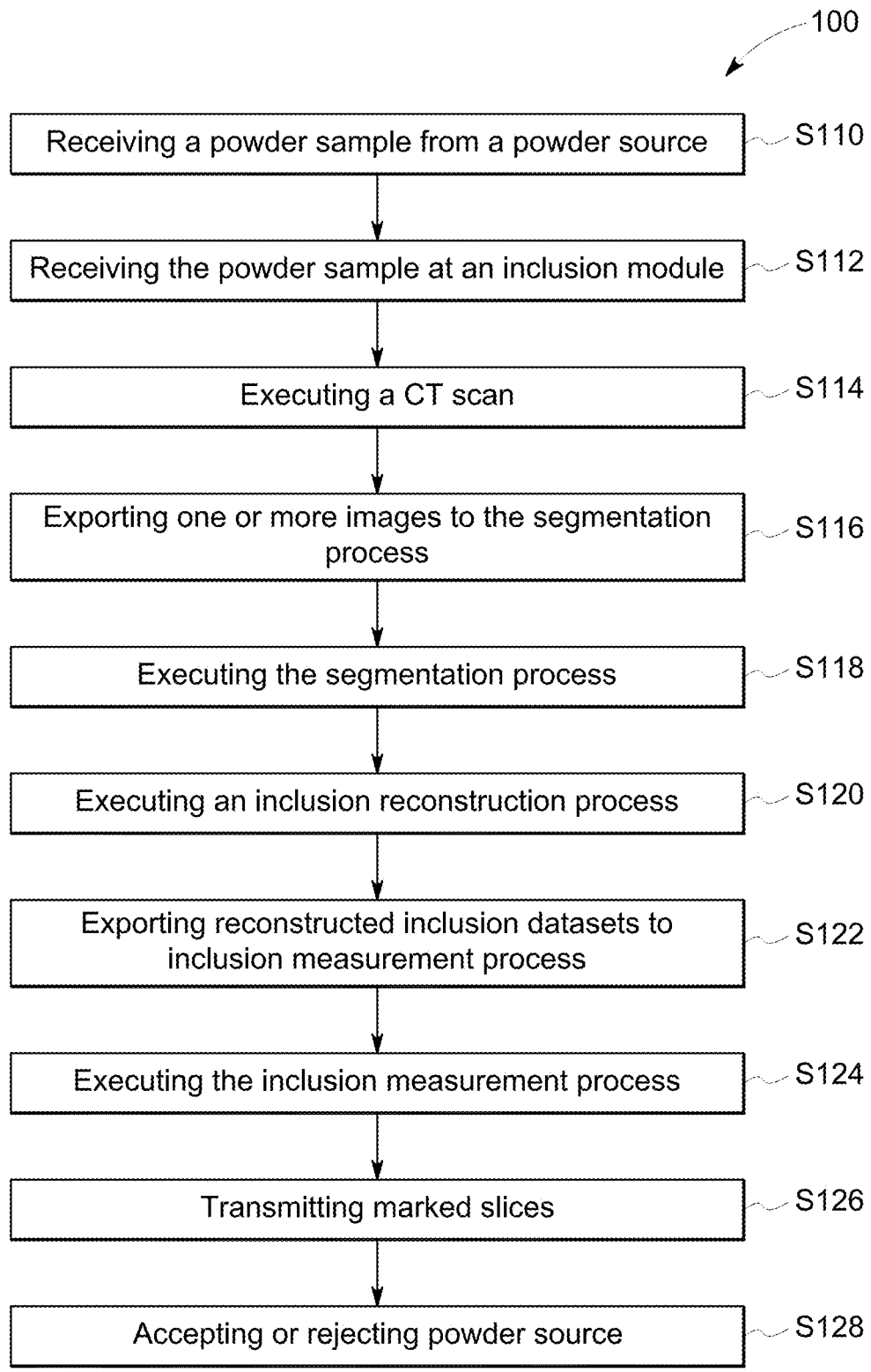
FIG. 1 illustrates a flow diagram according to some embodiments.

Industrial equipment or assets, generally, are engineered to perform particular tasks as part of industrial processes. For example, assets may include, among other things and without limitation, manufacturing equipment on a production line, aircraft engines, wind turbines that generate electricity on a wind farm, power plants, locomotives, health care and/or imaging devices (e.g., X-ray or MRI systems) or surgical suites for use in patient care facilities or drilling equipment for use in mining operations.

Powder metals may be used to create various components of industrial assets or equipment such as aircraft engine components (disks, blades, nozzles, etc.). Typically, to make the metallic components of these assets ("metallic components"), a metallic powder, which may be an alloy or single metallic element, may be tested for contaminants, as described below. As used herein, the terms "metallic powder" and "powder" may be used interchangeably. After the powder has been approved for use via the testing, the powder may be placed into a vessel (e.g., a can), from which it is processed into a consolidated form such as a solid stick. Other suitable consolidated forms may be used. The solid stick may then be cut into pieces, which are in turn forged into various components of the metallic component (e.g., components of an engine). It is noted that while the metallic component may operate at a high temperature due to the properties of the metal, the metallic component may operate at a lower temperature. As a non-exhaustive example, a specific engine component such as the disk or blade can operate at high temperature during take-off/landing conditions, but at much lower temperature during cruise condition.)

The powder metal may include some level of defects that may originate as contamination in the powder. Even very low levels of defects may be detrimental to the properties of the metallic component made from the powder metals. The mechanical capability of an alloy may be limited by the level of defects. As a non-exhaustive example, a metallic component (e.g., a disk for an aircraft engine) is made from powder metal that has an inclusion. If that inclusion is at a location within the metallic component that experiences high stress (e.g., "high stress point") during operation cycles, a crack will eventually form at this high stress location, which may lead to metallic component failure.

As such, there are current methods to detect or quantify metal powder contamination, such that the powder may be processed to remove the contaminant or that the powder may be discarded.

A current method to quantify metal powder contamination is by Heavy Liquid Separation (HLS), a method that utilizes a Thallium-containing high-density liquid to separate the most common contaminants (e.g. Alumina) from the bulk of the powder metal. The HLS method allows for the quantification of low density inclusions and/or process contaminants which can float in a liquid having a higher density while the metal separates by sinking because the metal has even higher density than the liquid. However, HLS is expensive, toxic and is limited to contaminant particles with lower densities than the heavy liquid. As such, HLS cannot find contaminants that are heavier than the density of the heavy liquid. For example, HLS is not suitable for newer alloys containing high density (or heavy) elements such as Hafnium, which is intentionally added to the alloy to improve mechanical properties. Hafnia therefore may be a new source of contamination leading to inclusions in the alloy, limiting material capability. It is also noted that much of the HLS cost may be related to processing of toxic chemicals (e.g., Thallium-containing).

It is noted that other detection methods may be used to detect gross contamination in metal powders, such as metal powders for Additive Manufacturing dispersed and fixed in a polymer. Unlike these additive powders, the following embodiments describe a high cleanliness powder, such as Premium Quality Alloy powders. A difference being the premium quality alloy powders are typically used in the most challenging rotating engine components such as disks where there is stringent requirement on allowable foreign inclusion contamination, thus a rigorous quality control method to inspect incoming metal powder cleanliness is imperative.

In one or more embodiments, an inclusion module may take a sample of loose powder and use a Computed Tomography (CT) process to scan the powder to find, if they exist, inclusions with densities both higher or lower than the density of the bulk metal powder. It is noted that in some embodiments, the inclusion module may be used in addition to HLS or as an alternative method. As a non-exhaustive example, Alumina may be difficult to distinguish from porosity in bulk powder. As such, if only the CT scanning process was used, the powder may need be turned into a consolidated form before the inclusion was detected. It is noted that detecting the inclusions in loose powder may be less expensive than detecting the inclusions in the generated metal component, as if the loose powder contains the inclusion, the inclusions may be removed before the expense of producing a metal component with inclusions, which may result in the metal component being unusable.

Figure 2:
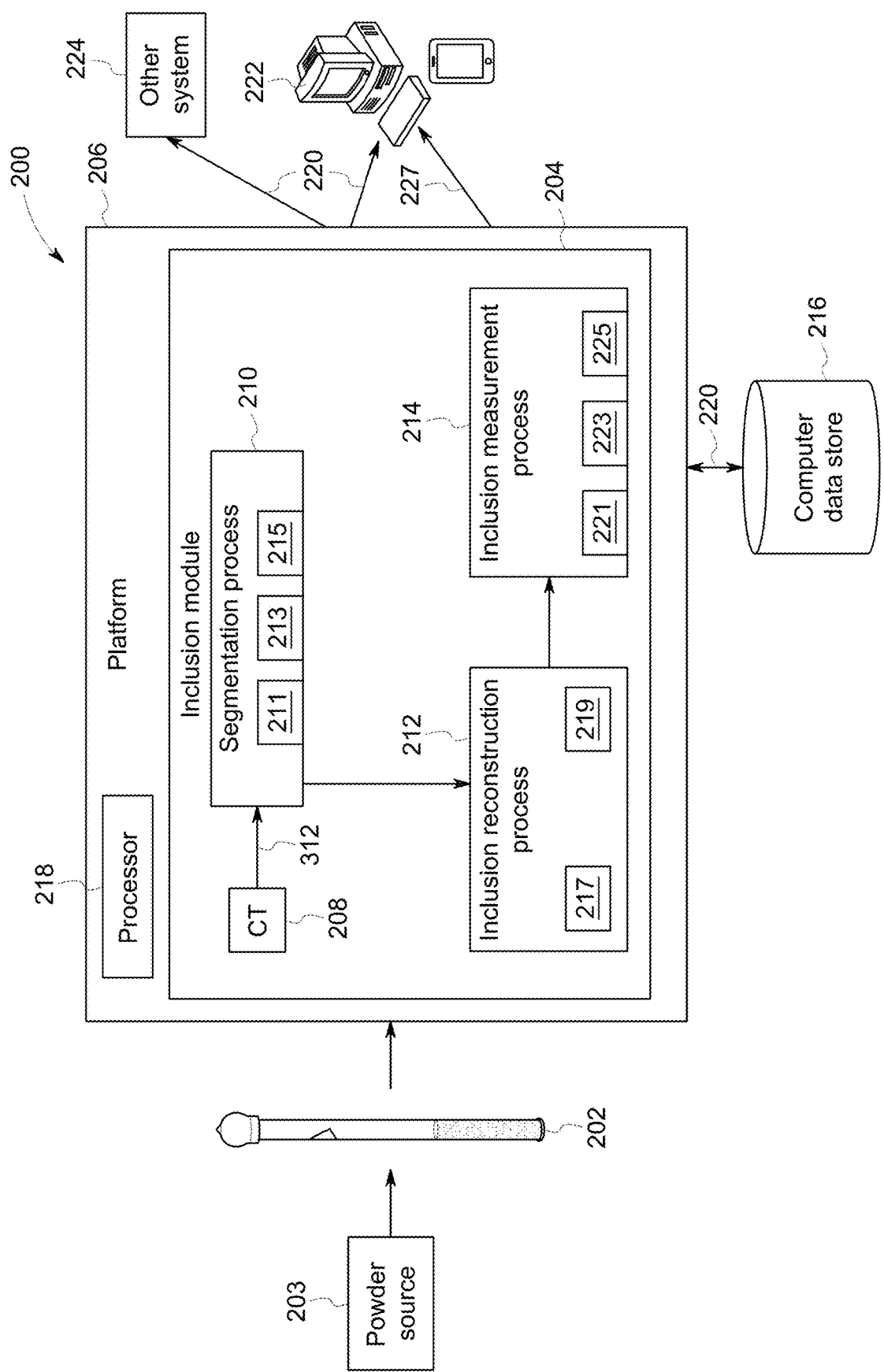
FIG. 2 illustrates a system according to some embodiments.
Figure 3:
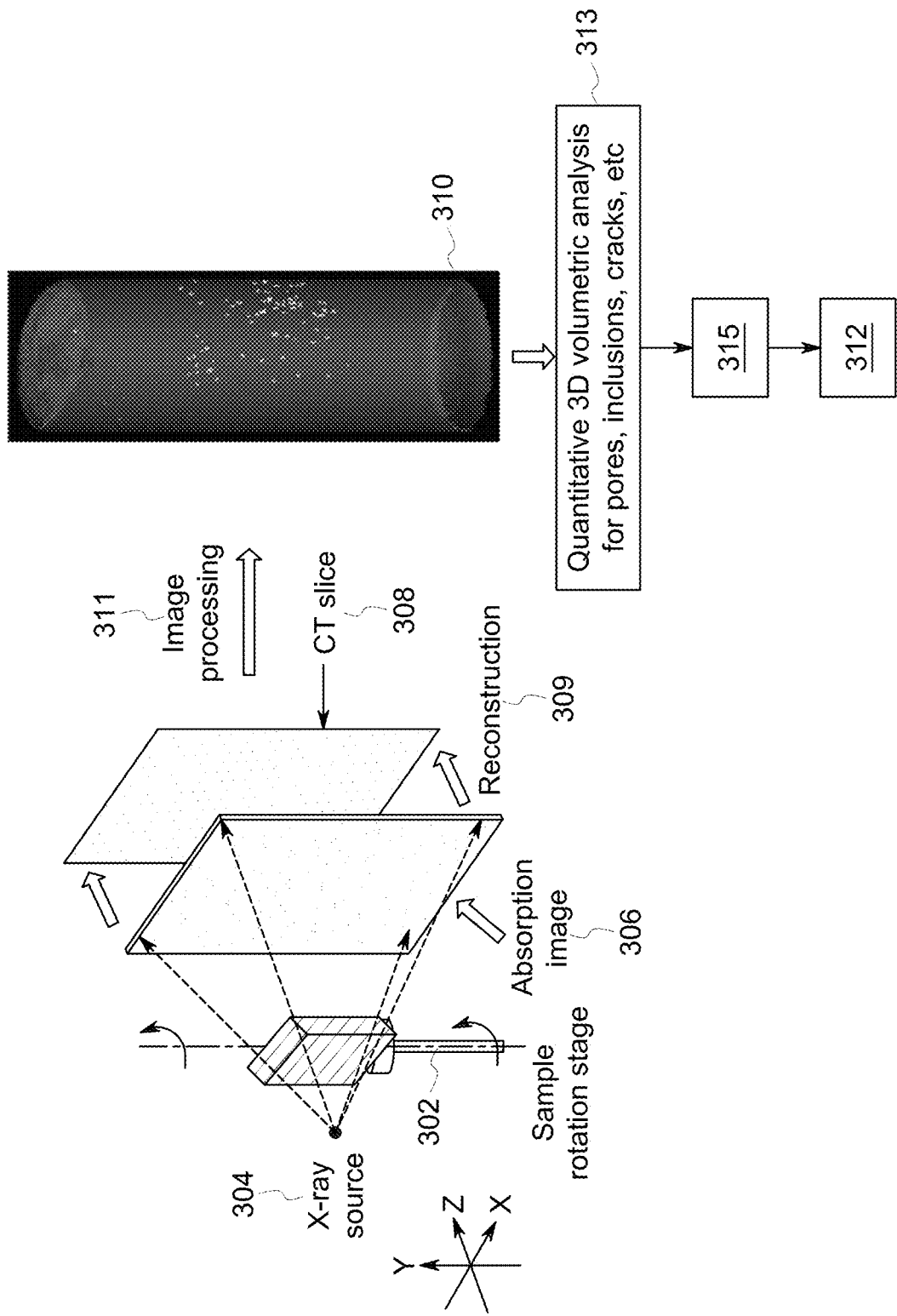
FIG. 3 illustrates a micro-computed tomography images.

Turning to FIGS. 1-3, flow diagram 100 (FIG. 1) and associated diagrams, of an example of operation according to some embodiments is provided. In particular, FIG. 1 provides a flow diagram of a process 100, according to some embodiments. Process 100, and any other process described herein, may be performed using any suitable combination of hardware (e.g., circuit(s)), software or manual means. For example, a computer-readable storage medium may store thereon instructions that when executed by a machine result in performance according to any of the embodiments described herein. In one or more embodiments, the system 200 is conditioned to perform the process 100 such that the system is a special-purpose element configured to perform operations not performable by a general-purpose computer or device. Software embodying these processes may be stored by any non-transitory tangible medium including a fixed disk, a floppy disk, a CD, a DVD, a Flash drive, or a magnetic tape. Examples of these processes will be described below with respect to embodiments of the system, but embodiments are not limited thereto. The flow chart(s) described herein do not imply a fixed order to the steps, and embodiments of the present invention may be practiced in any order that is practicable.

Initially, at S110, a metal powder sample 202 ("powder sample") is received from a powder source 203. It is noted that in one or more embodiments, the powder sample 202 may be received directly from the powder source 203 or may be pre-processed (e.g., sieving) after receipt from the powder source 203. It is noted that the form of powder sources may include loose powder and powders after consolidation such as, but not limited to, Hot Isostatic Processing (HIP) and Spark Plasma Sintering (SPS). It is further noted that while CT and the following process may be used for both powder and consolidated powders, the use of a consolidated powder may make the following process longer, more difficult to correct for inclusions, and may introduce additional contamination through the consolidation process. The powder source 203 may be a Premium Quality Nickel Superalloys for Aircraft Rotating Parts, or any other suitable powder source. In one or more embodiments, a subset of the powder source 203 may be removed therefrom for analysis, where the subset is representative for the whole/larger amount of powder in the powder source 203. As a non-exhaustive example, a quarter pound subset of the powder source 203 may be used as a representative sample 202. Other suitable quantities may be used as a subset/sample. The subset of powder may then be further split into one or more scanning vessels to provide the powder sample 202. The scanning vessel may be test tube or any other suitable vessel. As a non-exhaustive example, the subset of powder may be split into one or more test tubes.

Then at S112, the powder sample 202 may be received at an inclusion module 204 on a platform 206. The inclusion module 204 may include a CT scan process 208, a segmentation process 210, an inclusion reconstruction process 212, and an inclusion measurement process 214. It is noted that the segmentation process 210, inclusion reconstruction process 212 and inclusion measurement process 214, may be automated and processed in batch mode for multiple datasets to increase analysis throughput.

At S114, the CT scan process 208 may be executed to generate one or more 3D images of the powder sample 202. The CT scan process 208 may be executed via a VTomex M300 or any other suitable micro-CT scan program system. During the CT scan process 208, data is acquired from x-ray images of the powder sample 202. In one or more embodiments, during the CT scan process 208, the powder sample 202 is placed on a rotation stage 302 (FIG. 3). The powder sample 202 is then exposed to an X-ray source 304 as it rotates 360 degrees on the rotation stage 302 and a series (e.g., more than one) of absorption images 306 are generated. The series of absorption images may be referred to as the absorption image dataset 307. Difference in gray scales in the absorption images 306 of the absorption image dataset 307 may indicate the density differences in the powder sample. The absorption images 306 may be at a high resolution (e.g., <1 mil or 25 um) via use of a Micron-size focal spot per a micro-CT. Other suitable CT scans may be used. Then an imaged volume is reconstructed from the absorption images 306 of the absorption image dataset 307 using a reconstruction process 309 including but not limited to back projection algorithms or other suitable algorithms such as iterative reconstruction. The results of the reconstruction process 309 may be a 3-D CT image dataset in the reconstructed volume that is a map of attenuation coefficients in the material. It is noted that the 3-D CT image dataset may include a series of 2D images (e.g., one of which is shown at 308) that may become 3D. An image processing process 311 may further process (e.g., alignment and data pre-processing) the 3D CT image data set to generate a quantitative 3D volume 310 for Quantitative 3D volumetric analysis 313 (e.g., analysis of pores, inclusions, cracks, etc.). It is noted that the inclusion needs to have a contrast difference from the surrounding matrix material to be detected by CT. Contrast in CT is created by the difference in Z (atomic number) and/or density, and is seen in FIG. 3 as the greyscale difference in the images.

The output of the Quantitative 3D volumetric analysis 313 may be one or more analyzed 3D images 315. It is noted that the analyzed 3D image volume 315 may be re-sliced into 2D slices (312) along a user-chosen orientation which may be defined by the user via entry in a user interface after reconstruction and alignment. As part of the Quantitative 3D volumetric analysis 313, X-ray measurements are taken of the powder sample from one or more different angles to produce cross-sectional images of specific areas of the scanned powder sample, allowing the user to see inside the object without cutting.

Then at S116, the one or more analyzed images (i.e. at least one of: one or more of the analyzed 2D images 312 and one or more of the analyzed 3D images 315), may be exported to the segmentation process 210, using image analysis software such as FIJI®. Other suitable software may be used. Segmentation of images (e.g., slices) may include, but is not limited to, adjusting image contrast, de-noising the images (e.g., gaussian blur), identifying the region of interest from the background, detection of differences in image intensity (e.g., adaptive thresholding, neural network), and application of other image kernel operations (e.g., dilation, erosion) to produce a simplified or labeled set of image slices highlighting features of interest. Other suitable segmentation processes may be used, including use of alternative image processing software. In S118, the segmentation process 210 may be executed to detect both low- and high-density inclusions. Before the detection, as part of the segmentation process 210, 2D images may be generated from the one or more analyzed 3D images 315. Next, as part of the segmentation process 210, inclusions (both low- and high-density) may be detected in the generated 2D images 211. For example, both alumina (low-density) and hafnia (high-density) may be detected by the segmentation process 210. In one or more embodiments, the segmentation process 210 may be automatic. In one or more embodiments, after the inclusions are detected, each of the detected inclusions may be categorized into a low-density group 213 and a high-density group 215 based on whether the inclusion has brighter contrast than the matrix material (high-density) or darker than the matrix material (low-density) using an algorithm to detect intensity differences within the image (e.g., adaptive thresholding, neural network). During the segmentation process 210, other qualities of the inclusions may be detected, including but not limited to, size of the inclusion (e.g., a 3D size), shapes of inclusions, and number of inclusions per unit volume.

Then in S120, the inclusion reconstruction process 212 is executed using software such as Dream3D. Other suitable inclusion reconstruction processes may be used. The inclusion reconstruction process 212 may receive the segmented image data (i.e., at least one of: one or more of the analyzed 2D image(s) 312 and one or one or more of the analyzed 3D images 315) from the segmentation process 210. Next the inclusion reconstruction process 212 may identify the segmented inclusions in the received images based on the identified inclusions from the segmentation process and generate one or more 3D representations 217 of each inclusion. The inclusion reconstruction process 212 may also filter noise and generate a 3-D mesh representation 219 for each inclusion (e.g., Stereolithography file or STL file).

These reconstructed mesh inclusion datasets 219 (e.g., 3-D mesh representation files) may then be exported to the inclusion measurement process 214 in S122. Next in S124, the inclusion measurement process 214 is executed, using an algorithm written in a scripting language such as Python, or any other suitable software. The inclusion measurement process 214 may include a size filtering process 221 for each inclusion; an inclusion size process 223 to determine a size of the inclusion, such as maximum cross-sectional area for each inclusion; a shape fitting process 225 to fit a shape, such as an ellipsoid (or any other suitable shape; e.g., convex hull), to the inclusion 217. In one or more embodiments, the size filtering process 221 may filter the inclusions 217 by size such that a sub-set of inclusions are available for further analysis. For example, size filtering process 221 may be set to filter the inclusions 217 to be less than 30 um in length. Then, for the sub-set of inclusions 217, the shape fitting process 225 is executed to calculate a best-fit shape for each inclusion 217 to obtain metrics that define the inclusions such as size and location. The results of the size filtering process 221, the inclusion size process 223 and the shape fitting process 225 may be written to a file, and inclusions 217 meeting particular parameters (size, shape, filter) may be marked (e.g., highlighted) on one or more analyzed 3D image slices 315 and/or on one or more 2-D image slices 312, where the slices are taken through the oriented 3-D volume to expose the maximum cross-sectional areas for further analysis by at least one of the users or other system for manual verification if desired. In one or more embodiments, the inclusions 217 in the filtered sub-set of inclusions (e.g., inclusions that are the result of the size filtering process 221, the inclusions size process 223 and the shape fitting process 225) may be ranked by size. For example, even if a number of small inclusions are included in the powder sample, they may not be of a size that is significant to accepting or rejecting the powder source. However, certain sized inclusions may be marked for further analysis.

The marked image slices 227 are then transmitted in S126. In one or more embodiments, the marked image slices 227 may be received by at least one of the user or another system for further analysis. Based on the further analysis, it may be determined whether the powder source 203 is accepted (e.g. not contaminated) or rejected (e.g., contaminated) in S128. In one or more embodiments, the determination may be based on the one or more marked image slices 227 and associated inclusion measurement information (e.g., size, shape, etc.) that may be used to quantify the degree of contamination, such that the degree of contamination is based on the one or more marked images. In one or more embodiments, the further analysis may include, but is not limited to, ensuring the segmentation appears adequate, and performing manual segmentation if necessary to get inclusion size (area).

It is noted that FIG. 2 represents a logical architecture for describing processes according to some embodiments, and actual implementations may include more or different components arranged in other manners.

In one or more embodiments, the system 200 may also include a computer data store 216 that may provide data to the inclusion module 204 and may also store results from the inclusion module 204. The platform 206 may include at least one processing element 218.

The processor 218 may, for example, be a conventional microprocessor, and may operate to control the overall functioning of the inclusion module 204.

The data store 216 may comprise any one or more systems that store data that may be used by the module. The data stored in data store 216 may be received from disparate hardware and software systems associated with the powder source 203, or otherwise, some of which are not interoperational with one another. The systems may comprise a back-end data environment employed in a business, industrial, or personal context. The data may be pushed to data store 216 and/or provided in response to queries received therefrom.

In one or more embodiments, the data store 216 may comprise any combination of one or more of a hard disk drive, RAM (random access memory), ROM (read only memory), flash memory, etc. The data store 216 may store software that programs the processor 218 and the inclusion module 204 to perform functionality as described herein.

The data store 216 may support multi-tenancy to separately support multiple unrelated clients by providing multiple logical database systems which are programmatically isolated from one another.

The data may be included in a relational database, a multi-dimensional database, an eXtendable Markup Language (XML) document, and/or any other structured data storage system. The physical tables of data store 216 may be distributed among several relational databases, multi-dimensional databases, and/or other data sources. The data of data store 216 may be indexed and/or selectively replicated in an index.

The data store 216 may implement as an "in-memory" database, in which volatile (e.g., non-disk-based) storage (e.g., Random Access Memory) is used both for cache memory and for storing data during operation, and persistent storage (e.g., one or more fixed disks) is used for offline persistency of data and for maintenance of database snapshots. Alternatively, volatile storage may be used as cache memory for storing recently-used database data, while persistent storage stores data. In some embodiments, the data comprises one or more of conventional tabular data, row-based data stored in row format, column-based data stored in columnar format, time series data in a time series data store, and object-based data. Data store 216 may store data used by applications. The data store may comprise any query-responsive data source or sources that are or become known, including but not limited to a structured-query language (SQL) relationship.

A communication channel 220 may be included in the system 200 to supply input from data store to the competence module 204.

In some embodiments, the system 200 may also include a communication channel 220 to supply output (e.g., datasets with marked inclusions) from the inclusion module 204 to at least one of: user platforms 222, or to other systems 224. In some embodiments, received output from the module 204 may cause modification in the state or condition of the powder source 203 (e.g., accepted for forging into components, rejected, or needs further processing to remove inclusions).

As used herein, devices, including those associated with the system 200 and any other devices described herein, may exchange information and transfer input and output ("communication") via any number of different systems. For example, wide area networks (WANs) and/or local area networks (LANs) may enable devices in the system to communicate with each other. In some embodiments, communication may be via the Internet, including a global internetwork formed by logical and physical connections between multiple WANs and/or LANs. Alternately, or additionally, communication may be via one or more telephone networks, cellular networks, a fiber-optic network, a satellite network, an infrared network, a radio frequency network, any other type of network that may be used to transmit information between devices, and/or one or more wired and/or wireless networks such as, but not limited to Bluetooth access points, wireless access points, IP-based networks, or the like. Communication may also be via servers that enable one type of network to interface with another type of network. Moreover, communication between any of the depicted devices may proceed over any one or more currently or hereafter-known transmission protocols, such as Asynchronous Transfer Mode (ATM), Internet Protocol (IP), Hypertext Transfer Protocol (HTTP) and Wireless Application Protocol (WAP).

A user may access the system 200 via one of the user platforms 222 (a control system, a desktop computer, a laptop computer, a personal digital assistant, a tablet, a smartphone, etc.) to view information about and/or manage the powder source 203 in accordance with any of the embodiments described herein.

Figure 4:
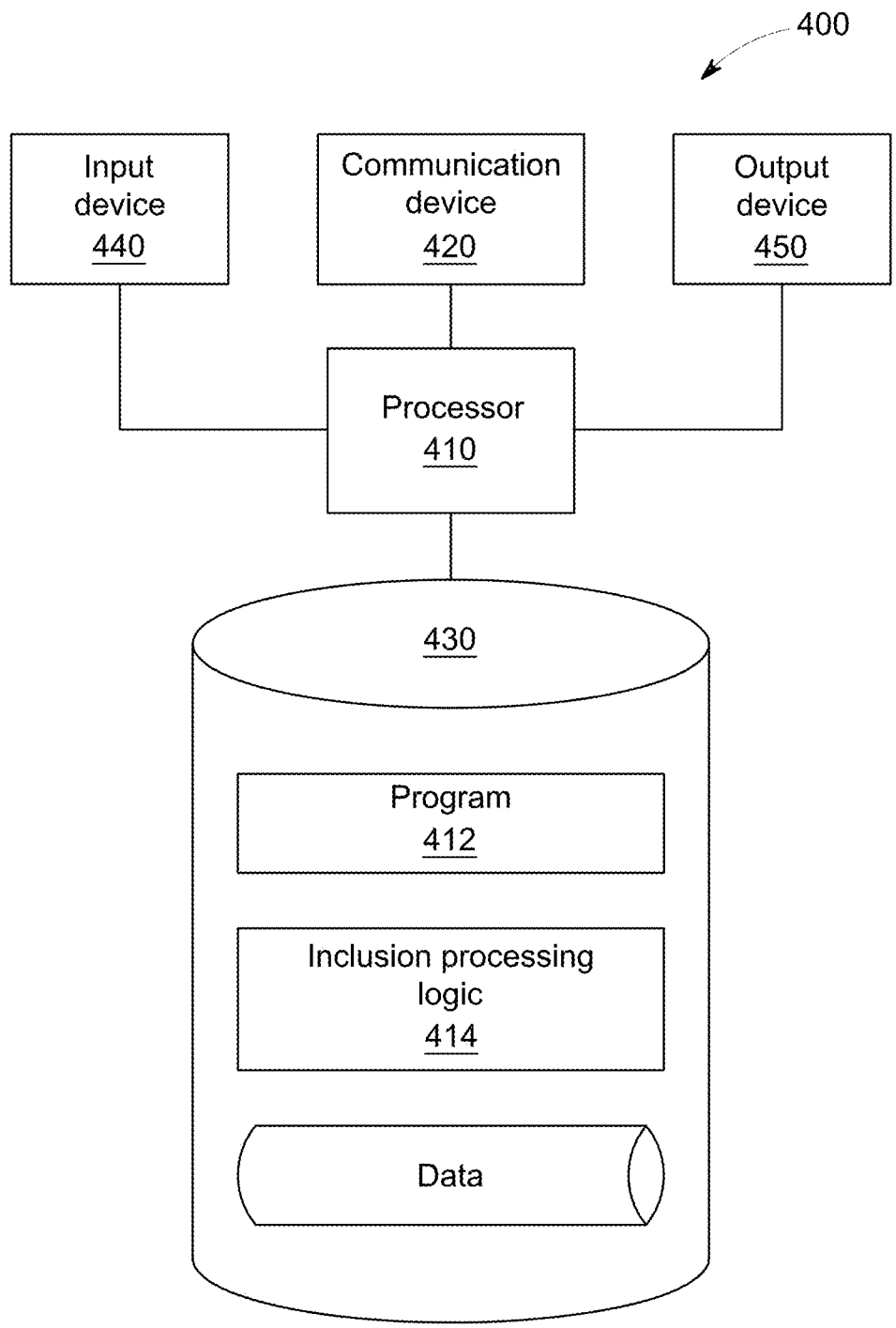
FIG. 4 illustrates a block diagram of a system according to some embodiments.

Note the embodiments described herein may be implemented using any number of different hardware configurations. For example, FIG. 4 illustrates an inclusion platform 400 that may be, for example, associated with the system 200 of FIG. 2. The inclusion platform 400 comprises an inclusion processor 410 ("processor"), such as one or more commercially available Central Processing Units (CPUs) in the form of one-chip microprocessors, coupled to a communication device 420 configured to communicate via a communication network (not shown in FIG. 4). The communication device 420 may be used to communicate, for example, with one or more users. The inclusion platform 400 further includes an input device 440 (e.g., a mouse and/or keyboard to enter information) and an output device 450 (e.g., to output the outcome of module execution).

The processor 410 also communicates with a memory/storage device 430. The storage device 430 may comprise any appropriate information storage device, including combinations of magnetic storage devices (e.g., a hard disk drive), optical storage devices, mobile telephones, and/or semiconductor memory devices. The storage device 430 may store a program 412 and/or inclusion processing logic 414 for controlling the processor 410. The processor 410 performs instructions of the programs 412, 414, and thereby operates in accordance with any of the embodiments described herein. For example, the processor 410 may receive data and then may apply the instructions of the programs 412, 414 to determine whether there are inclusions and whether the found inclusions should be marked.

The programs 412, 414 may be stored in a compressed, uncompiled and/or encrypted format. The programs 412, 414 may furthermore include other program elements, such as an operating system, a database management system, and/or device drivers used by the processor 410 to interface with peripheral devices.

As used herein, information may be "received" by or "transmitted" to, for example: (i) the platform 400 from another device; or (ii) a software application or module within the platform 400 from another software application, module, or any other source.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein. The method steps can then be carried out using the distinct software modules and/or sub-modules of the system, as described above, executing on one or more hardware processors 410 (FIG. 4). Further, a computer program product can include a computer-readable storage medium with code adapted to be implemented to carry out one or more method steps described herein, including the provision of the system with the distinct software modules.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

The invention claimed is:
1. A system comprising:
an inclusion module to receive a powder sample from a powder source;
a computed tomography equipment;
a memory for storing program instructions;

an inclusion processor, coupled to the memory, and in communication with the inclusion module, and operative to execute program instructions to:
receive the powder sample;
execute a computed tomography (CT) scan process of the received powder sample to generate a first dataset including one or more images;
identify inclusions in the one or more images, via a segmentation process;
reconstruct, via a reconstruction process, the identified inclusion into a 3D representation;
measure the identified inclusion;
mark the inclusions on one or more image slices from the 3D representations; and
determine whether the powder source is contaminated based on the one or more marked images.

2. The system of claim 1, wherein the inclusions are one of high density inclusions and low density inclusions.

3. The system of claim 2, further comprising program instructions to:
categorize the identified inclusion as a high density inclusion or a low density inclusion.

4. The system of claim 1, wherein an image volume is reconstructed from the first dataset prior to the segmentation process.

5. The system of claim 4, wherein the image volume is analysed via a quantitative 3D volumetric analysis.

6. The system of claim 5, wherein the segmentation process generates one or more images prior to identification of the inclusions.

7. The system of claim 1, wherein the reconstruction process generates a 3D mesh representation for each inclusion.

8. The system of claim 1, wherein the measurement of the identified inclusion includes at least one of a size filtering process, an inclusion size process and a shape fitting process.

9. The system of claim 1, wherein the marked inclusions are ranked in size.

10. A method comprising:
receiving a powder sample from a powder source;
executing a computed tomography (CT) scan process of the received powder sample to generate a first dataset including one or more images;
identifying inclusions in the one or more images, via a segmentation process;
reconstructing, via a reconstruction process, the identified inclusion into a 3D representation;
measuring the identified inclusion;
marking the inclusions on one or more image slices from the 3D representations; and
determining whether the powder source is contaminated based on the one or more marked images.

11. The method of claim 10, wherein the inclusions are one of high density inclusions and low density inclusions.

12. The method of claim 11, further comprising:
categorizing the identified inclusion as a high density inclusion or a low density inclusion.

13. The method of claim 10, further comprising:
reconstructing an image volume from the first dataset prior to the segmentation process.

14. The method of claim 13, further comprising:
analysing the image volume via a quantitative 3D volumetric analysis.

15. The method of claim 14, further comprising:
generating, via the segmentation process, one or more 2D images prior to identification of the inclusions.

16. The method of claim 10, further comprising:
generating a 3D mesh representation for each inclusion.

17. The method of claim 10, wherein measuring the inclusion includes at least one of a size filtering process, an inclusion size process and a shape fitting process.

18. A non-transient, computer-readable medium storing instructions to be executed by a processor to perform a method comprising:
receiving a powder sample from a powder source;
executing a computed tomography (CT) scan process of the received powder sample to generate a first dataset including one or more images;
identifying inclusions in the one or more images, via a segmentation process;
reconstructing, via a reconstruction process, the identified inclusion into a 3D representation;
measuring the identified inclusion;
marking the inclusions on one or more image slices from the 3D representations; and
determining whether the powder source is contaminated based on the one or more marked images.

19. The medium of claim 18 further comprising:
categorizing the identified inclusion as a high density inclusion or a low density inclusion.

20. The medium of claim 18, further comprising:
reconstructing an image volume from the first dataset prior to the segmentation process.

\* \* \* \* \*